United States Patent
Ferro

(10) Patent No.: US 10,543,000 B2
(45) Date of Patent: Jan. 28, 2020

(54) RECIPROCATING SURGICAL SAW BLADE

(71) Applicant: AOD Holdings, LLC, Arroyo Grande, CA (US)

(72) Inventor: Thomas Ferro, Arroyo Grande, CA (US)

(73) Assignee: AOD HOLDINGS, LLC, Arroyo Grande, CA (US)

( * ) Notice: Subject to any disclaimer, the term of this patent is extended or adjusted under 35 U.S.C. 154(b) by 471 days.

(21) Appl. No.: 15/202,167

(22) Filed: Jul. 5, 2016

(65) Prior Publication Data

US 2017/0027586 A1 Feb. 2, 2017

Related U.S. Application Data

(60) Provisional application No. 62/188,245, filed on Jul. 2, 2015.

(51) Int. Cl.
*A61B 17/14* (2006.01)

(52) U.S. Cl.
CPC .................. *A61B 17/142* (2016.11)

(58) Field of Classification Search
CPC .................................................. A61B 17/142
See application file for complete search history.

(56) References Cited

U.S. PATENT DOCUMENTS

| | | | |
|---|---|---|---|
| 4,513,742 A * | 4/1985 | Arnegger | B23D 61/006 30/350 |
| 5,403,318 A | 4/1995 | Boehringer et al. | |
| 5,409,491 A * | 4/1995 | Boehringer | B23D 59/04 606/178 |
| 5,507,763 A | 4/1996 | Petersen et al. | |
| 5,569,257 A | 10/1996 | Amegger et al. | |
| 5,846,244 A | 12/1998 | Cripe | |
| 7,691,106 B2 * | 4/2010 | Schenberger | A61B 17/142 606/82 |
| 8,852,221 B2 | 10/2014 | Boykin et al. | |
| 8,920,424 B2 | 12/2014 | Boykin | |

FOREIGN PATENT DOCUMENTS

WO 2014083525 A2 6/2014

* cited by examiner

*Primary Examiner* — Nicholas W Woodall
(74) *Attorney, Agent, or Firm* — McDonnell Boehnen Hulbert & Berghoff LLP

(57) ABSTRACT

A reciprocating surgical saw blade includes a distal portion, a proximal portion, and a main body extending between the distal portion and the proximal portion. The main body includes an upper surface and a lower surface, and a first outer edge extending from the upper surface to the lower surface of the main body, and a second outer a second outer edge extending from the upper surface to the lower surface of the main body. A biocompatible polymer is provided along at least one of the upper surface, the lower surface, the first outer edge, or the second outer edge of the main body.

16 Claims, 3 Drawing Sheets

FIG. 8

RECIPROCATING SURGICAL SAW BLADE

CROSS REFERENCE TO RELATED APPLICATION

The present application claim priority to U.S. Provisional patent application 62/188,245, filed on Jul. 2, 2015, and entitled "Wear Reducing Cutting System," which is herein incorporated by reference as if fully set forth in this description.

FIELD OF THE PRESENT DISCLOSURE

This present disclosure relates to surgical cutting system and components. More specifically, the present disclosure relates to a reciprocating surgical saw blade that prevents abrasions that may occur between a reciprocating surgical saw blade and a cutting guide slot, thereby helping to ensure bone cutting precision while also reducing undesired surgical debris.

BACKGROUND

Orthopedic related surgeries often require repositioning/partial removal of bone. One of the commonly used tools to cut or prepare the bone is a reciprocating surgical saw blade. This practice is more common in a joint replacement surgery. A joint replacement surgery is a procedure in which the arthritic or dysfunctional joint surface is replaced with an orthopedic prosthesis. Joint replacement is considered as a treatment when there is severe joint pain or dysfunction is not alleviated by less-invasive therapies.

In a joint replacement surgery, a reciprocating saw blade is one of the various instruments which are used for cutting the bone. The saw blades have teeth on their cutting edge so as to facilitate cutting through the bone. During such a surgery, the reciprocating a saw blade is fitted in a motor driven power tool to cut the measured section of the bone. The saw blade when connected to a motor driven power tool may oscillate in a back and forth and sideways oscillating motion. To enhance precision in cutting the measured section of the bone, the saw blade is used in conjunction with a cutting guide that is fixed or pinned around the target anatomy so that the bone is precisely cut along the lines of the slot.

The surgeon performs the surgical procedure by sequentially inserting the saw blade in the slot. Once the blade is inserted in the slot, the saw is actuated by the power tool. In this manner the surgeon is able to cut the bone along the precisely defined lines along which the bone is to be separated. The blade cuts the bone where its motion range is constrained by the walls of metal cutting guide slot. Such an interface of the blade and walls of the cutting guide slot gives rise to friction which can increase the heat and debris, thereby affecting the outcome of the surgery. Debris generated increases the potential of osteolysis and eventually bone loss around the affected region. Friction may also unnecessarily consume the power supplied to the saw blade. The wearing of the blade can also widen the slot thereby affecting the accuracy of the cut. This means that the slot and/or blade must be repaired or replaced with a new one which in turn may again affect the accuracy and also increase the overall cost. In the long run, excessive wear may affect the accuracy of the cutting guide, in which case life of the cutting guide is compromised.

In certain orthopedic procedures, the instruments used to resect bone can produce instances where particulate metal debris can be formed by the action of passing a reciprocating or oscillating surgical saw blade through a cutting guide. Even though steps are taken to ensure that dissimilar metals and coatings are used, there is still a propensity for both microscopic and macroscopic metal debris to form. This debris can find its way into the joint cavity/capsule of the patient. This debris will then be present in the patient post-surgery, where it may have a possibility of becoming lodged in either bone tissue or soft tissue in the knee joint, or where the saw was utilized. The local effect of metal debris that remains in the patient can eventually lead to osteolysis and implant loosening or bone resorption.

There is, therefore, a general need to reduce undesired debris that can be generated during a surgical procedure while also maintaining accuracy and precision in the cutting of the measured section of the bone during an orthopedic surgery. There is also a general need to reduce friction at the interface between the blade and the walls of cutting guide slot used during an orthopedic surgery, thereby reducing undesired metal particles so as to prevent osteolysis.

SUMMARY

In one arrangement, a reciprocating surgical saw blade is provided. The reciprocating surgical saw blade comprises, a distal portion, a proximal portion, and a main body extending from the distal portion to the proximal portion. The main body comprising an upper surface and a lower surface, and a first outer edge extending from the upper surface to the lower surface of the main body, and a second outer edge extending from the upper surface to the lower surface of the main body. A biocompatible polymer disposed along at least one of the upper surface, the lower surface, the first outer edge, or the second outer edge of the main body of the reciprocating surgical saw blade.

In one reciprocating surgical saw blade arrangement, the biocompatible polymer comprises a sheath that is disposed along the upper surface, the lower surface, the first outer edge, and the second outer edge of the main body of the reciprocating surgical saw blade. In one arrangement, the sheath extends from the distal portion to the proximal portion of the reciprocating surgical saw blade. As just one example, the sheath may comprise a solid sheath that extends from the distal portion to the proximal portion of the reciprocating surgical saw blade.

In one reciprocating surgical saw blade arrangement, either the upper surface or the lower surface of the main body of the reciprocating surgical saw blade comprises at least one recessed surface, wherein the biocompatible polymer resides within the at least one recessed surface. In one example, the biocompatible polymer residing within the at least one recessed surface may be flush or may not be flush with an upper surface of the distal portion of the reciprocating surgical saw blade. In addition, the at least one recessed surface defines a plurality of cavities.

In one reciprocating surgical saw blade arrangement, the reciprocating surgical saw blade may comprise a cutting geometry provided along a distal end face of the distal portion of the reciprocating surgical saw blade.

In one reciprocating surgical saw blade arrangement, the reciprocating surgical saw blade may comprise at least one elastic barrier running along either the first outer edge or the second outer edge of the main body of the reciprocating surgical saw blade. The at least one elastic barrier may be configured to dampen a force received from the reciprocating surgical saw blade when the blade comes into contact with a cutting guide. For example, the at least one elastic barrier may extend from the distal portion to the proximal portion of the reciprocating saw blade.

In one reciprocating surgical saw blade arrangement, the main body of the reciprocating surgical saw blade defines a plurality of cavities, wherein each cavity extends between the upper surface and the lower surface of the main body.

In one reciprocating surgical saw blade arrangement, the reciprocating surgical saw blade may comprise at least one elongated cavity provided either along the upper surface or the lower surface of the main body of the reciprocating surgical saw blade, wherein the biocompatible polymer is disposed within the at least one elongated cavity. For example, the at least one elongated cavity extends between the upper surface and the lower surface of the main body.

In one reciprocating surgical saw blade arrangement, the biocompatible polymer provided along at least one surface of the main body of the reciprocating surgical saw blade is flush with an upper surface of the distal portion of the reciprocating surgical saw blade.

In one reciprocating surgical saw blade arrangement, the distal portion comprises a distal portion height $H_{DP}$ that is different than a main body portion height $H_{MB}$ of the main body of the reciprocating surgical saw blade.

In one reciprocating surgical saw blade arrangement, the reciprocating surgical saw blade may comprise a distal portion, a proximal portion, and a main body extending between the distal portion and the proximal portion. The main body may comprise an upper surface and a lower surface, and a first outer edge extending from the upper surface to the lower surface, and a second outer a second outer edge extending from the upper surface to the lower surface. The reciprocating surgical saw blade may further comprise at least one elastic barrier running along either the first outer edge or the second outer edge of the main body of the reciprocating surgical saw blade. The at least one elastic barrier is configured to dampen a force received from the reciprocating surgical saw blade when the reciprocating surgical saw blade comes into contact with a cutting guide. For example, the at least one elastic barrier may comprise an elongated slot, the elongated slot extending between the upper surface and the lower surface of the main body of the reciprocating surgical saw blade.

In one reciprocating surgical saw blade arrangement, the reciprocating surgical saw blade may comprise a biocompatible polymer provided along at least one of the upper surface, the lower surface, the first outer edge or the second outer edge of the main body of the reciprocating surgical saw blade.

In one reciprocating surgical saw blade arrangement, the reciprocating surgical saw blade may comprise, either the upper surface or the lower surface of the main body of the reciprocating surgical saw blade comprises at least one recessed surface, wherein the biocompatible polymer resides within the at least one recessed surface. As just one example, the biocompatible polymer residing within the at least one recessed surface may or may not be flush with an upper surface of the distal portion of the reciprocating surgical saw blade.

In one reciprocating surgical saw blade arrangement, at least one recessed surface defines a plurality of cavities.

The disclosed reciprocating surgical saw blade arrangements provide numerous additions and enhancements. For example, disclosed surgical blade arrangements enable a reciprocating surgical blade to have less contact with another metal surfaces, such as a metal surface provided by cut guides. In addition, disclosed surgical blade arrangements also help to mitigate impact related damage or metal debris, from orthopedic cut guides. Typically, the use of oscillating surgical saw blades results in certain friction wear of the broad contact surfaces. This broad contact can develop microscopic metal debris that can be seen by the naked eye in the form of black smudges on the patient's resected bone tissue. Also, there is a tendency for the rigid metal edges of the saw blade to impact upon the interior edges of cut guide. This can potentially develop a buildup of burrs that can detach from the cut guides and end up in the patient.

The disclosed reciprocating surgical blade saw arrangements limits this with a twofold approach. First, in one reciprocating surgical blade saw arrangement, there is a thin layer of a biocompatible polymer or other friction and wear reducing coating, but not limited to, that acts as an intermediate friction reducing layer. When contact between the surgical blade saw and guide occurs, and wear of one or both also will typically occur, it is on behalf of the biocompatible polymer layer instead of the metal material that the saw blade is comprised of. In one arrangement, the biocompatible polymer layer may also wrap around to the edges of the saw blade, where the biocompatible polymer can act as a buffer to the impact forces created by the oscillation of the blade in the cut guide.

In an alternative arrangement, this impact buffering could also be achieved with a narrow slot or a plurality of slots running down the outboard edges of the reciprocating saw blade main body. These slots would create a thin area on the edge of the reciprocating saw blade that could compress and rebound to limit the impact force of the blade edge within the cut guide.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

Exemplary embodiments are described herein with reference to the drawings, in which.

DETAILED DESCRIPTION

Figure 1:
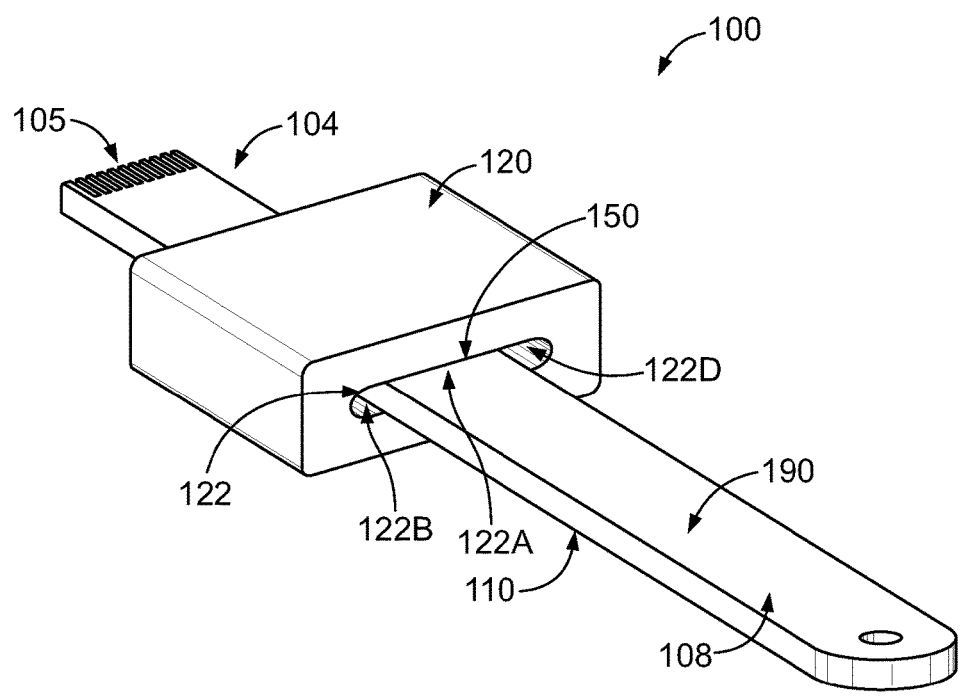
FIG. 1 illustrates a surgical cutting system that includes a reciprocating saw blade in combination with a cutting guide.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present disclosure relates to a bone cutting surgical device, such as a reciprocating saw blade. The device is able to engage with powered surgical instruments via proximal connection points on the proximal end of the cutting device. Once connected, the cutting device may oscillate side to side or back and forth. In one arrangement, the device will have a sleeve comprised of a biocompatible polymer material. This friction reducing coating will act as an intermediate wear reduction surface that will mitigate the broad surface metal on metal contact that typically occurs when in use in conjunction with a cutting guide.

In one arrangement, the reciprocating saw blade comprises a recessed surface so that the friction reducing coating surface geometry will sit flush with the broad metal surface of the blade body. Also, the reciprocating saw blade can have a series of slots running along the outer edge of the metal body to act as an elastic barrier to dampen the force received from the metal on metal contract the cutting device receives from the metal cutting guide. This can also be enhanced, or replaced, by a side relief where the friction reducing material comprises the outer perimeter of the blade that is most likely to contact the cut guide walls with an oscillating motion. The features that reduce the blade vibration also improves accuracy of the resection.

For example, FIG. 1 illustrates a surgical cutting system 100 that includes a reciprocating surgical saw blade 110 in combination with a surgical cutting guide 120. As illustrated, the saw blade 110 has a first or distal portion or end 104. The saw blade 100 further comprises a second end or proximal end or portion 108. Preferably, the first end or distal end/portion 104 comprises a plurality of teeth 105. As will be described in greater detail herein, in one preferred arrangement, the saw blade 110 comprises a biocompatible polymer 140 that is provided along at least one surface of the saw blade 100.

As illustrated, prior to a cutting surgical procedure, the saw blade 110 is inserted into a cutting guide slot 150 defined by the surgical cutting guide 120. The cutting guide slot 120 defines a top surface 122A, a bottom surface 122B, and two side walls 122 C,D. During a cutting procedure, a motorized tool will oscillate the saw with the cutting guide slot 120 so as to guide the saw along a targeted cut path. The oscillating motion of the saw will drive the reciprocating saw blade, and allow it to make cuts in bone tissue with the cutting geometry provided along a distal end face of the saw. This cutting geometry can vary as needed based upon the desired cutting action and force. Materials and certain procedures may dictate other changes to blade cutting geometry or thickness.

The proximal portion 108 of the reciprocating saw blade 110 is configured to be connected to a motor driven power tool which can be of any shape compatible with the motor driven power tool to derive the power to cut the bone. During this bone cutting procedure, interferences can occur between the inner surfaces of the cutting guide and the various surfaces of the reciprocating saw. The biocompatible polymer 140 of the blade helps to minimize friction that may be generated by the interfaces occurring between the oscillating saw blade surfaces and the inner surfaces of the cutting guide slot.

Figure 2:
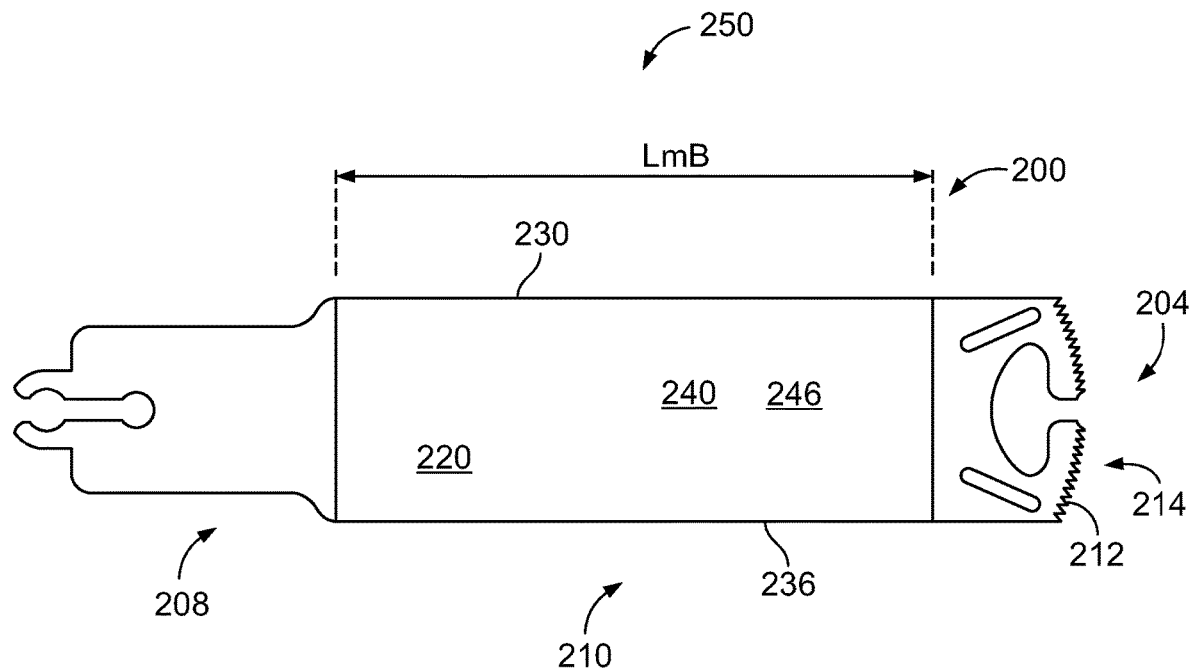
FIG. 2 shows a top down view of a reciprocating saw blade arrangement.
Figure 3:
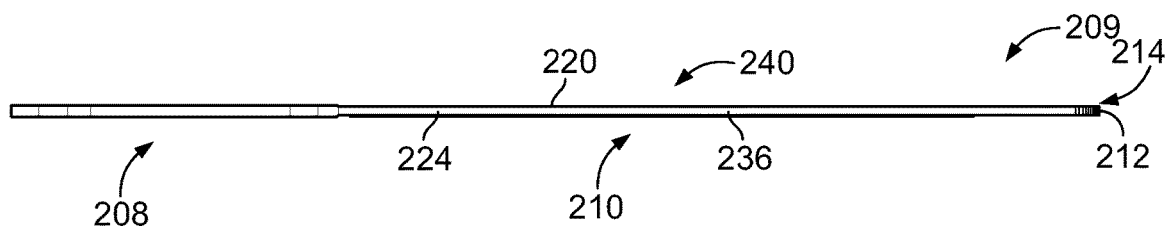
FIG. 3 illustrates a side view of the reciprocating saw blade arrangement illustrated in FIG. 1.

FIG. 2 shows a top down view of a reciprocating saw blade arrangement 200 for use with a surgical cutting system 100, such as the surgical cutting system 100 illustrated in FIG. 1. FIG. 3 illustrates a side view of the reciprocating saw blade arrangement 200 illustrated in FIG. 1. Referring now to FIGS. 2 and 3, the reciprocating saw blade arrangement 200 comprises a distal portion or a first portion 204 and a proximal portion or a second portion 208. The blade arrangement 200 further comprises a main body 210 that extends from the distal portion 204 to the proximal portion 208. A cutting geometry 214 is provided along a distal end face 212 of the distal portion 204 of the reciprocating surgical saw blade 200. Such a cutting geometry 214 may comprise a plurality of cutting teeth.

The main body 210 comprises an upper or a top surface 220 and a lower or a bottom surface 224. The main body 210 further also comprises a first outer edge 230 that extends from the upper surface of the main body 210 to the lower surface 224 of the main body 210. Similarly, the main body 210 further comprises a second outer edge 236 extending from the upper surface 220 to the lower surface 224 of the main body 210. The illustrated blade saw arrangement 200 also comprises a biocompatible polymer 240 that disposed along at least one surface of the blade saw. That is, the illustrated blade saw arrangement 200 comprises a biocompatible polymer 240 that is disposed along at least one of the upper surface 220, the lower surface 224, the first outer edge 230, or the second outer edge 236 of the main body 210 of the reciprocating surgical saw blade 200.

As just one example, the biocompatible polymer 240 may comprise a sheath or a prophylactic coating 246 that surrounds the main body 210 or at least a portion of the main body 210. Such a sheath may be disposed along the both the upper surface 220, the lower surface 224, the first outer edge 230, and the second outer edge 236 of the main body 210 of the reciprocating surgical saw blade 200. Such a sheath 246 may extend along the entire length $L_{MB}$ 250 of the main body 210 of the surgical saw blade 200. In one exemplary arrangement, the sheath 246 may extend from the distal portion 204 to the proximal portion 208 of the reciprocating surgical saw blade 210. Alternative sheath arrangements may also be used. As just one example, the sheath 246 may extend only along a portion of the length $L_{MB}$ 250 of the main body 210. Alternatively, one or more sheaths may be utilized along the length $L_{MB}$ 250 of the main body 210 of the surgical saw 200.

Figure 4:
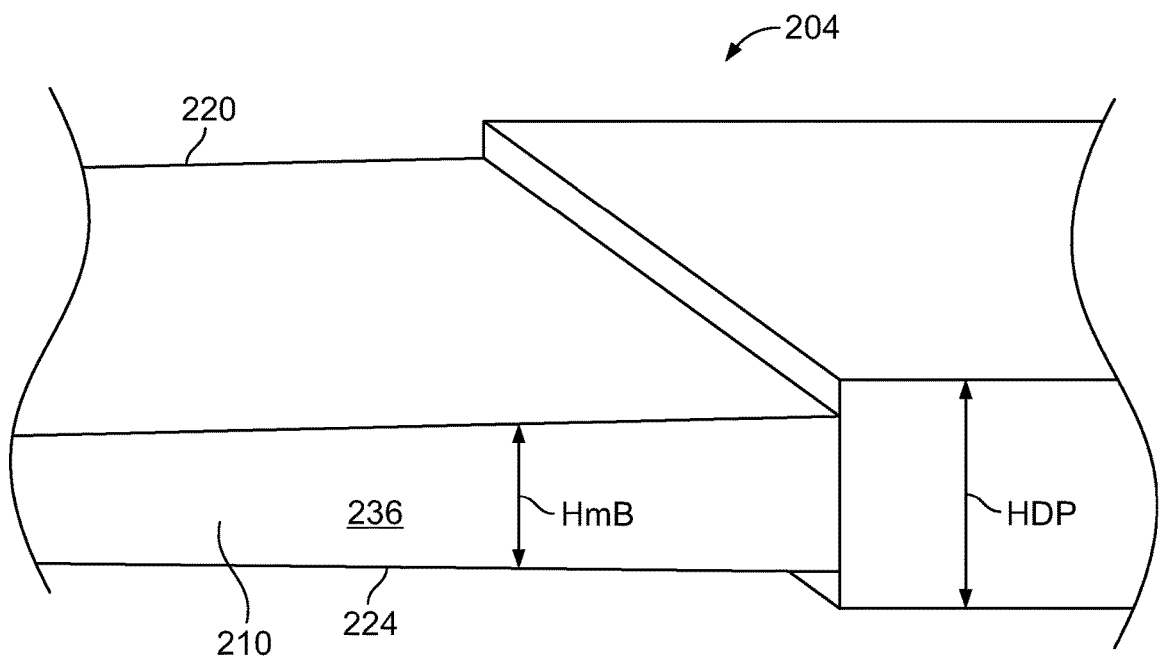
FIG. 4 illustrates a close up view of a portion of the reciprocating saw blade illustrated in FIGS. 1 and 2.
Figure 5:
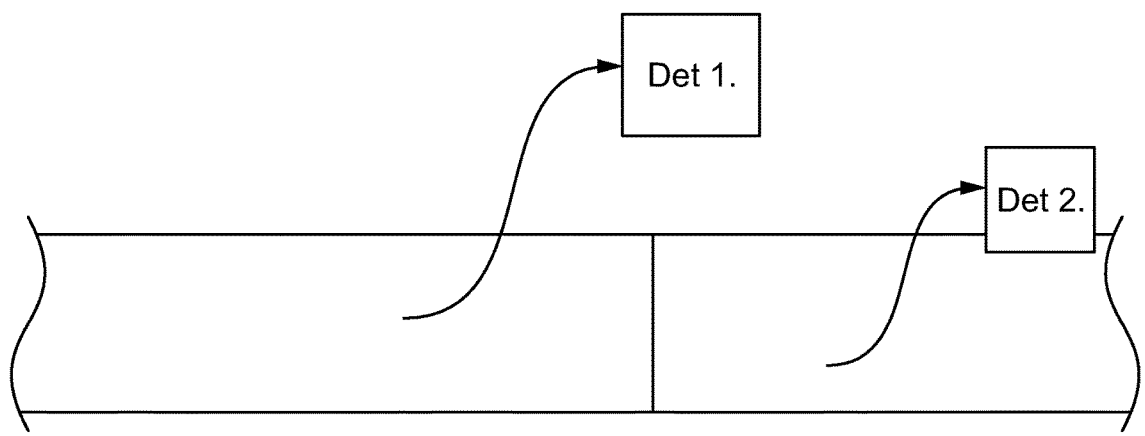
FIG. 5 shows a detail view of the recess that allows for the polymer material to be flush, or even to the surface of the metal blade. Detail 1*a* is the polymer material, and detail 2*a* is the distal end portion of the reciprocating saw blade.

In one exemplary arrangement, the sheath 246 comprises a solid sheath that extends from the distal portion 204 to the proximal portion 208 of the reciprocating surgical saw blade 200. In one exemplary arrangement, the sheath 246 is flush with a top surface of the distal portion 204 of the reciprocating saw 200. For example, FIG. 4 illustrates a close up view of the main body 210 and the distal portion 204 of the reciprocating saw 200 illustrated in FIGS. 2 and 3. As illustrated, a the distal portion 204 comprises a distal portion height $H_{DP}$ that is different than a main body portion height $H_{MB}$ of the main body 210 of the reciprocating surgical saw blade 200. Specifically, in one arrangement, the distal portion 204 comprises a distal portion height $H_{DP}$ that is larger than a main body portion height $H_{MB}$ of the main body 210 of the reciprocating surgical saw blade. As such, in this arrangement, a polymer provided along the outer surfaces of the main body 210 would then be flush with the outer surfaces of the distal portion 204. For example, FIG. 5 shows a detail view of the recess that allows for the polymer material to be flush, or even to the surface of the saw blade. Detail 1 *a* is the polymer material 240, and detail 2 *a* is the distal end portion 204 of the reciprocating saw blade 210.

Figure 6:
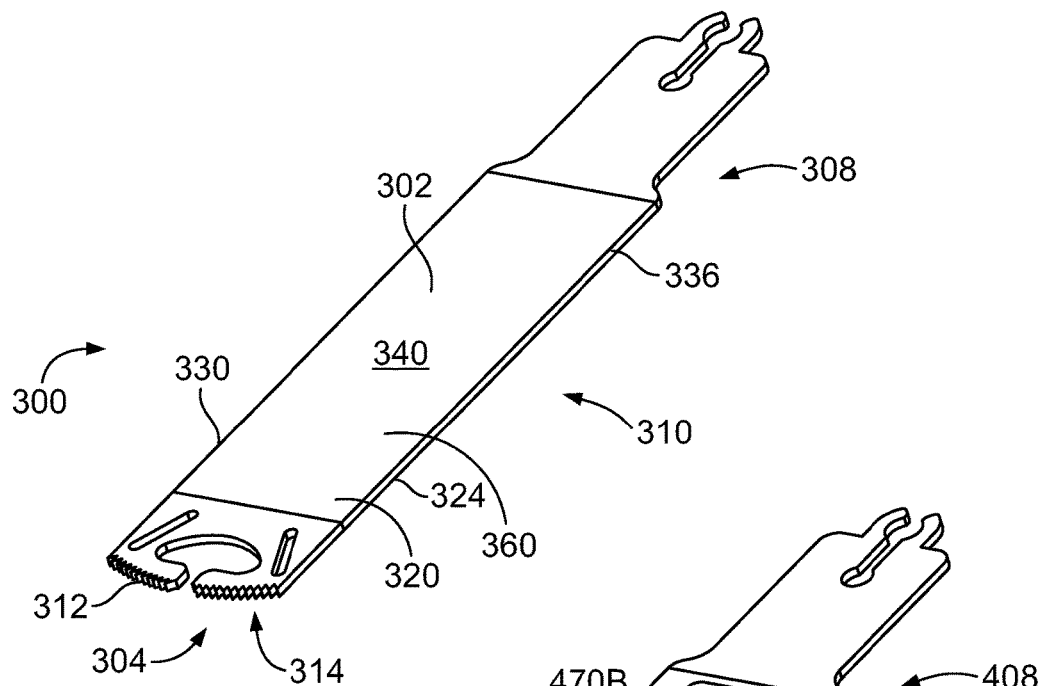
FIG. 6 illustrates a perspective view of another reciprocating saw blade arrangement.

In one exemplary arrangement, the main body 210 of surgical saw arrangement 200 may define a plurality of cavities. For example, FIG. 6 illustrates an alternative surgical saw arrangement 300 comprising a plurality of cavities 302. Similar to the arrangement 200 illustrated in FIGS. 1 and 2, surgical saw arrangement 300 comprises a distal portion or a first portion 304 and a proximal portion or a second portion 308. The blade arrangement 300 further comprises a main body 310 that extends from the distal portion 304 to the proximal portion 308. A cutting geometry 314 is provided along a distal end face 312 of the distal portion 304 of the reciprocating surgical saw blade 300. Such a cutting geometry 314 may comprise a plurality of cutting teeth.

The main body 310 comprises an upper or a top surface 320 and a lower or a bottom surface 324. The main body 310 further also comprises a first outer edge 330 that extends from the upper surface 320 of the main body 310 to the lower surface 324 of the main body 310. Similarly, the main body 310 further comprises a second outer edge 336 extending from the upper surface 320 to the lower surface 324 of the main body 310. The illustrated blade saw arrangement 300 also comprises a biocompatible polymer 340 that is disposed along at least one surface of the blade saw 300. That is, the illustrated blade saw arrangement 300 comprises a biocompatible polymer 340 that is disposed along at least one of the upper surface 320, the lower surface 324, the first outer edge 330, or the second outer edge 336 of the main body 310 of the reciprocating surgical saw blade 300. In addition, the main body 310 defines a plurality of cavities 302 that extend between the upper surface 320 and the lower surface 324 of the main body 310. As just one example, cavity 360 extends between the upper surface 320 and the lower surface 324 of the main body 310.

Figure 7:
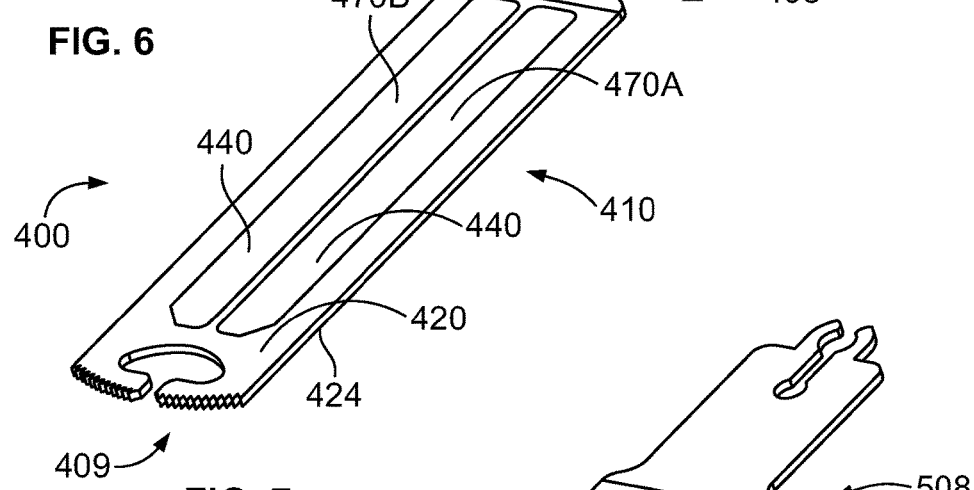
FIG. 7 illustrates a perspective view of another reciprocating saw blade arrangement.

FIG. 7 illustrates an alternative arrangement surgical saw arrangement 400. Similar to the arrangement 200 illustrated in FIGS. 2 and 3, the arrangement 400 illustrated in FIG. 7 comprises a distal portion 404, a proximal portion 408, a main body 410 extending from the distal portion 304 to the proximal portion 408. The main body 410 comprises an upper surface 420 and a lower surface 424, and a first outer edge 430 extending from the upper surface to the lower surface of the main body 410, and a second outer edge 436 extending from the upper surface 420 to the lower surface 424 of the main body 410. In addition, the reciprocating surgical saw blade 400 may comprise one or more recessed surfaces 470. As illustrated, the reciprocating surgical saw blade 400 comprises two recessed surfaces 470 A,B provided along the upper or top surface 420 of the reciprocating surgical saw blade 400. One or more recessed surfaces may also be provided along a bottom surface of the reciprocating surgical saw blade 400. In one preferred arrangement, a biocompatible polymer 440 is provided to reside within the at least one recessed surface.

The biocompatible polymer 440 residing within the recessed surface or surfaces 470 A,B may or may not be flush with an upper surface of the distal portion 404 of the reciprocating surgical saw blade 400. That is, a height defined by the biocompatible polymer 440 residing with the recessed surface 470 A,B may have a height greater than a height defined by the distal portion 404 of the reciprocating surgical saw blade 400. One reason for providing for such a height difference is that where contact occurs between the blade and the guide (such as the guide illustrated in FIG. 1), it will be the biocompatible polymer 440 that experiences friction and not the metal of the saw blade 400.

In one arrangement, the recessed surface 470 A,B may also define a plurality of cavities 480. Such cavities may aid with the formation and/or adhesion of a biocompatible polymer 440 along the surfaces of the main body 410.

In one arrangement, the reciprocating surgical saw blade 400 illustrated in FIG. 7 may further comprise at least one elastic barrier running along either the first outer edge 430 or the second outer edge 436 of the main body 410 of the reciprocating surgical saw blade 400. For example, such the at least one elastic barrier can be configured to dampen a force received from the reciprocating surgical saw blade when the blade comes into contact with a cutting guide.

Figure 8:
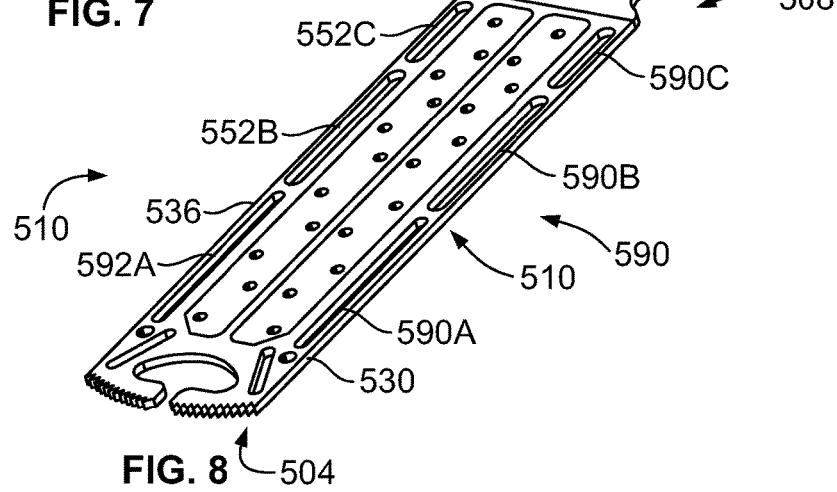
FIG. 8 illustrates a perspective view of yet another reciprocating saw blade arrangement.

For example, FIG. 8 illustrates an alternative reciprocating surgical saw blade 500 comprising at least one elastic barrier 590. In this illustrated arrangement, three barriers 590 A,B,C are provided along a first edge 530 of the main body 510. Similarly, three barriers 592 A,B,C are provided along a second edge 536 of the main body 510. However, as those of ordinary skill in the art will recognize, alternative barrier arrangements may also be used. As just one example, an alternative reciprocating surgical saw blade may comprise at least one elastic barrier that extends from a distal portion 504 to a proximal portion 510 of the reciprocating saw blade 500.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

I claim:
1. A reciprocating surgical saw blade comprising:
   a distal portion,
   a proximal portion,
   a main body extending from the distal portion to the proximal portion, the main body comprising
      an upper surface and a lower surface,
      a first outer edge extending from the upper surface to the lower surface of the main body, wherein the first outer edge has a total surface area that is less than a total surface area of the upper surface and less than a total surface area of the lower surface, and
      a second outer edge extending from the upper surface to the lower surface of the main body, wherein the second outer edge has a total surface area that is less than a total surface area of the upper surface and less than a total surface area of the lower surface,
   wherein the upper surface extends a first distance from the distal portion to the proximal portion along a longitudinal axis of the reciprocating surgical saw blade and extends a second distance from the first outer edge to the second outer edge along an additional axis that intersects the longitude axis,
wherein the first distance is greater than the second distance, and
wherein the upper surface is recessed with respect to the distal portion and the proximal portion,
the reciprocating surgical saw blade further comprising a biocompatible polymer on the upper surface.

2. The reciprocating surgical saw blade of claim 1,
wherein the biocompatible polymer is raised with respect to an upper surface of the distal portion.

3. The reciprocating surgical saw blade of claim 1,
wherein the upper surface defines a plurality of cavities.

4. The reciprocating surgical saw blade of claim 1 further comprising a cutting geometry provided along a distal end face of the distal portion.

5. The reciprocating surgical saw blade of claim 1 further comprising,
an elastic barrier running along either the first outer edge or the second outer edge,
wherein the elastic barrier is configured to dampen a force received from the reciprocating surgical saw blade when the reciprocating surgical saw blade comes into contact with a cutting guide.

6. The reciprocating surgical saw blade of claim 5 wherein,
the elastic barrier extends from the distal portion to the proximal portion.

7. The reciprocating surgical saw blade of claim 1,
wherein the main body defines a plurality of cavities,
wherein each cavity of the plurality extends between the upper surface and the lower surface.

8. The reciprocating surgical saw blade of claim 1 further comprising
an elongated cavity provided either along the upper surface or the lower surface,
wherein the biocompatible polymer is disposed within the elongated cavity.

9. The reciprocating surgical saw blade of claim 8, wherein
the elongated cavity extends between the upper surface and the lower surface of the main body.

10. The reciprocating surgical saw blade of claim 1,
wherein the distal portion comprises a distal portion height $H_{DP}$ that is different than a main body portion height $H_{MB}$ of the main body.

11. The reciprocating surgical saw blade of claim 1,
wherein the upper surface of the distal portion.

12. A reciprocating surgical saw blade comprising:
a distal portion,
a proximal portion,
a main body extending between the distal portion and the proximal portion, the main body comprising
an upper surface and a lower surface, wherein the upper surface is recessed with respect to the distal portion and the proximal portion,
a first outer edge extending from the upper surface to the lower surface, and
a second outer edge extending from the upper surface to the lower surface, and
a first elastic barrier having a first end and a second end, the first elastic barrier running parallel to the first outer edge between the first end of the first elastic barrier and the second end of the first elastic barrier,
a second elastic barrier having a first end and a second end, the second elastic barrier running parallel to the first outer edge between the first end of the second elastic barrier and the second end of the second elastic barrier,
wherein the upper surface extends a first distance from the distal portion to the proximal portion along a longitudinal axis of the reciprocating surgical saw blade and extends a second distance from the first outer edge to the second outer edge along an additional axis that intersects the longitudinal axis,
wherein the first distance is greater than the second distance,
wherein the first end of the first elastic barrier faces the first end of the second elastic barrier, and
wherein the first elastic barrier and the second elastic barrier are configured to dampen a force received from the reciprocating surgical saw blade when the reciprocating surgical saw blade comes into contact with a cutting guide,
the reciprocating surgical saw blade further comprising a biocompatible polymer on the upper surface.

13. The reciprocating surgical saw blade of claim 12,
wherein the first elastic barrier comprises an elongated slot, the elongated slot extending between the upper surface and the lower surface.

14. The reciprocating surgical saw blade of claim 12,
wherein the biocompatible polymer is raised with respect to an upper surface of the distal portion.

15. The reciprocating surgical saw blade of claim 12,
wherein the upper surface defines a plurality of cavities.

16. The reciprocating surgical saw blade of claim 12,
wherein the biocompatible polymer is flush with an upper surface of the distal portion.

* * * * *